(12) United States Patent
Friebel et al.

(10) Patent No.: US 8,357,431 B2
(45) Date of Patent: Jan. 22, 2013

(54) USE OF AMINE-MODIFIED SILOXANES AS PROTECTING AGENTS FOR COATINGS AND WORKPIECES

(75) Inventors: Stefan Friebel, Evessen (DE); Claudia Philipp, Braunschweig (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 862 days.

(21) Appl. No.: 12/299,062

(22) PCT Filed: May 15, 2007

(86) PCT No.: PCT/DE2007/000878
§ 371 (c)(1),
(2), (4) Date: Jan. 16, 2009

(87) PCT Pub. No.: WO2007/131487
PCT Pub. Date: Nov. 22, 2007

(65) Prior Publication Data
US 2009/0304932 A1    Dec. 10, 2009

(30) Foreign Application Priority Data

May 17, 2006 (DE) .......................... 10 2006 023 415

(51) Int. Cl.
*B65B 33/00* (2006.01)
*C09D 5/20* (2006.01)
*B05D 1/02* (2006.01)
*B05D 1/18* (2006.01)
*A01N 59/04* (2006.01)
*A01N 63/00* (2006.01)

(52) U.S. Cl. ..... 427/294; 427/154; 427/155; 427/421.1; 427/427.4; 427/430.1; 504/101; 504/118; 504/148; 504/149

(58) Field of Classification Search ............... 427/154, 427/155, 170, 294, 350, 394, 421.1, 427.4, 427/430.1, 434.2, 445; 504/101, 118, 119, 504/148, 149, 187; 528/28, 29, 38
See application file for complete search history.

(56) References Cited

U.S. PATENT DOCUMENTS

| | | | |
|---|---|---|---|
| 2,930,809 A | 3/1960 | Kenmore et al. | |
| 3,389,160 A | 6/1968 | Reid et al. | |
| 4,359,545 A | 11/1982 | Ona et al. | |
| 4,541,936 A | 9/1985 | Ona et al. | |
| 4,615,706 A * | 10/1986 | Martin | 8/115.56 |
| 5,075,403 A * | 12/1991 | Kirk | 528/15 |
| 5,130,344 A | 7/1992 | Kollmeier et al. | |
| 5,464,900 A | 11/1995 | Stofko, Jr. et al. | |
| 5,565,518 A | 10/1996 | Stofko, Jr. | |
| 6,326,061 B1 * | 12/2001 | Lautenschlager et al. | 427/394 |
| 6,896,766 B2 * | 5/2005 | Sarbo et al. | 162/112 |
| 6,977,026 B2 * | 12/2005 | Liu et al. | 162/164.4 |
| 2003/0175438 A1 | 9/2003 | Reeve | |
| 2004/0228826 A1 | 11/2004 | Yamamoto et al. | |

FOREIGN PATENT DOCUMENTS

| | | |
|---|---|---|
| DE | 689 21 781 T2 | 4/1989 |
| DE | 3928867 C1 | 8/1989 |
| DE | 42 43 399 A1 | 12/1992 |
| DE | 197 39 991 A1 | 9/1997 |
| DE | 199 39 866 A1 | 8/1999 |
| DE | 100 24 270 A1 | 5/2000 |
| DE | 10 2004 036 717 A1 | 7/2004 |
| DE | 10 2004 049 427 A1 | 10/2004 |
| EP | 1 194 434 B1 | 6/2000 |
| EP | 0 862 858 B1 | 7/2002 |
| GB | 882069 | 3/1957 |

* cited by examiner

*Primary Examiner* — Michael Cleveland
*Assistant Examiner* — Michael Wieczorek
(74) *Attorney, Agent, or Firm* — Whitham Curtis Christofferson & Cook, PC

(57) ABSTRACT

The present invention relates to the use of certain amine-modified siloxanes, exhibiting at least one molecular unit with an amine-modified radical and at least one molecular unit with a hydrophilic radical, as protecting agents. These protecting agents are suitable for protecting materials, such as wood and other substances based on cellulose and/or lignin, but also other materials, such as plastics, minerals, and metals, from infestation by and spread of harmful microorganisms, such as fungi. The present invention further relates to a method of enhancing surfaces and workpieces, comprising the application and/or incorporation of the protecting agent of the invention to the surfaces and/or into the workpieces.

26 Claims, 4 Drawing Sheets

USE OF AMINE-MODIFIED SILOXANES AS PROTECTING AGENTS FOR COATINGS AND WORKPIECES

The present invention relates to the use of certain amine-modified siloxanes, exhibiting at least one molecular unit with an amine-modified radical and at least one molecular unit with a hydrophilic radical, as protecting agents. These protecting agents are suitable for protecting materials, such as wood and other substances based on cellulose and/or lignin, but also other materials, such as plastics, minerals, and metals, from infestation by and spread of harmful microorganisms, such as fungi. The present invention further relates to a method of enhancing surfaces and workpieces, comprising the application and/or incorporation of the protecting agent of the invention to the surfaces and/or into the workpieces.

BACKGROUND ART

Microorganisms, such as fungi or bacteria, are generally found on all surfaces which surround us in everyday life. Although the bacteria or fungi that are present on the surfaces are typically harmless to humans, there are high hygiene standards specifically in sensitive areas, such as in the food industry and in medicine, for example, these standards envisaging a very low microbe count. In these two areas specifically, microbe-free surfaces are required, which can be realized only through the use of microbicidal chemicals. Such surfaces are equipped, accordingly, with biocides, in order to prevent the uncontrolled propagation of microorganisms. Microorganisms require only minimal amounts of nutrients; for example, often just a few dust particles, with appropriate atmospheric humidity, may be sufficient for their growth. Therefore, numerous building materials, such as wood, plaster, stone, metals, and their coatings, for example, constitute a nutrient substrate for microorganisms. The microorganisms present not only are harmful to the persons that come into association with the surfaces of these building materials, but may also themselves contribute to the destruction of the building materials and hence of the built structures, by attacking and destroying the components and/or their protective coats.

Thus, for example, a mold infestation in interiors harbors a high allergenic and health risk. The allergenic effects of a number of species of mold are already known. In practice it is appropriate to adopt a policy of minimization, since even hitherto unobtrusive species may have a sensitizing effect. A further danger is formed by the molds which form mycotoxins.

The growth of the microorganisms is further promoted by external circumstances, such as high atmospheric humidity, especially in kitchens and bathrooms, minimal or absent ventilation of rooms, and also constructional circumstances, such as cupboards which stand close to the wall, etc. A further factor which contributes to an increased incidence of microorganisms in interiors is the improved insulation of the external walls and the windows. This leads to increased colonization of façades and internal walls by algae and fungi. The atmospheric moisture condenses on the cold walls and forms the conditions that are needed for growth.

To protect against microorganisms, the surfaces and articles are treated, in the event of damage or preventively, with biocidal chemicals. These chemicals are frequently compounds of low molecular mass, in many cases toxic to humans as well, which are applied directly or in solution. Typically these compounds, on account of their chemical structure and small size, penetrate into the cells of the microorganisms, where they alter structures and kill them off. These compounds, known as microbiocidal substances, are capable of killing off the microorganisms or, as microbiostatic substances, of inhibiting growth or propagation of the microorganisms, without killing off the microorganisms themselves. Microbicidal substances include algicides, bactericides, fungicides, etc.

In addition there is the class of the contact microbicides, which enter into contact only with the cell membrane of the microorganisms, where they influence the growth and the spread of the microorganisms. However, microbicides are typically used up in the surfaces over time, and therefore do not afford any lasting protection.

Amine-containing biocidal actives are known from the literature in the form, for example, of quaternary ammonium compounds (QUATS). They possess a broad spectrum of action with respect to fungi. The activity is based on the presence of at least one long alkyl chain on the nitrogen atom. This interacts with the cell surface of the microorganisms and thereby hinders their growth. QUATS are mostly water-soluble and are employed in aqueous solutions. It is, however, also conceivable to carry out functionalization of QUATS and to attach them covalently into a polymer, as proposed for example in EP 1 194 434 B1.

The activity of polymers with secondary amino functions has already been described. Thus it is apparent from EP 0 862 858 that copolymers of tert-butylaminoethyl methacrylate inherently possess microbicidal properties. DE 10024270 A1 describes antimicrobial polymers comprising alkylacrylamides, which, themselves or as a polymer blend, equip surfaces lastingly with antimicrobial action and, moreover, are resistant to solvents and physical stresses.

Amine-modified siloxanes are known for use as softeners in the textile industry. Among others, DE 197 39 991 A1 describes aminosiloxane-polyether polymers for textile treatment. The compounds are described for use as wetting agents and dispersants, additives in fabric softeners, or antifoam powders. The functional groups of the polymers described therein are connected via Si—C and via Si—O—C bonds. The process for preparing the aminosiloxane-polyether polymers described therein takes place through condensation reactions of various silanes—and/or siloxane starting materials and polyether glycols, with elimination of constituents of low molecular mass.

DE 3928867 describes amino-functional polysiloxane-polyoxyalkylene block copolymers for the cell opening of rigid polyurethane foams. U.S. Pat. No. 3,389,160 discloses organomodified siloxanes with dialkylamino- and hydroxy-functional groups. In contrast to the modified siloxanes described here, they do not contain hydrophilic groups, e.g., polyether-functional groups. The area of application of these molecules lies in corrosion control or as surfactants for aqueous systems. None of these documents describes an antimicrobial effect of these amine-modified polysiloxanes.

DE 68921781 describes organosilicon-containing quaternary ammonium compounds and their antimicrobial activity. The compounds in question, however, are silane compounds, and not polysiloxanes. DE 4243399, finally, describes organopolysiloxane compounds with guanidyl groups, which possess an antibacterial activity. Surface-active aspects remain unconsidered.

Furthermore, DE 199 39 866 and U.S. Pat. No. 4,541,936 disclose organopolysiloxanes in aqueous or organic compositions for the treatment of paper and/or wood and wood products. No microbicidal—fungicidal, for example—effect of the amine-modified siloxanes described therein is stated.

In relation to the prior art identified above, therefore, it is an object of the present invention to provide for the use of compounds in protecting agents, such as surface-coating systems, which protect surfaces of workpieces or the workpieces themselves, examples being lignocellulosic materials, such as wood and woodbase materials, from microbial infestation.

DESCRIPTION OF THE INVENTION

The present invention relates to the use of amine-modified siloxanes in protecting agents with microbicidal effects, such as in surface-coating systems for protecting surfaces. More exactly, the present invention relates to the use of the amine-modified siloxanes as protecting agents in coating systems and workpieces, such as wood, with which it is possible to improve the resistance with respect to microbial infestation.

The protecting agent used in accordance with the invention is directed more particularly for wood and woodbase materials, chipboard, medium-density fiberboard, OSB boards, paper, cardboard packaging, lignocellulose-based insulating boards, plywood, and veneers, which are referred to below collectively as lignocellulosic materials. Other workpieces too, however, such as those made of metals, plastics, minerals, etc., can be treated with the amine-modified siloxanes of the invention and suitable coating systems. Alternatively the amine-modified siloxanes of the invention may be used in polymer systems or in binders for the production of workpieces, in order to prevent or halt microbial infestation. On account of the functional radicals of the amine-modified siloxanes of the invention, these siloxanes accumulate in the surface regions of the workpieces.

The amine-modified siloxanes which can be used in accordance with the invention, also referred to below as amine-modified polysiloxanes or else as aminosilicones, have a microbicidal, such as a fungicidal, or microbiostatic, such as a fungistatic, activity. These amine-modified polysiloxanes possess at least one molecular unit with an amine-modified radical, and at least one molecular unit with a hydrophilic radical, it being possible if appropriate for these two radicals to be present on one molecular unit. It has surprisingly been found, indeed, that siloxanes which have been modified with these two radicals, the amine-modified radical and the hydrophilic radical, such as a polyether radical, in addition to antimicrobial, and especially fungistatic, properties, are present, partly owing to their surfactant-like structure, in a state of distribution in the workpiece or coating such that the amine-modified siloxanes of the invention are present at a higher concentration at the surface of the treated workpiece or coating than in the remaining region of the workpiece or coating. Furthermore, these compounds do not contain substances of low molecular mass which, as a result of migration, represent environmentally problematic substances. Instead, as a result of the specific structure of the molecule and the surfactant-like character formed as a result, namely the simultaneous presence of hydrophilic and hydrophobic groups, there is an accumulation and optimum orientation of the molecule at the surface of the coating system, such as of the surface-coating system, and so only a small amount thereof is needed in the coating system in order to achieve the microbicidal activity. Accordingly the compounds of the invention are specifically not in homogeneous distribution in the coating or the treated workpiece.

Conventional biocides are admixed homogeneously to coating materials typically in a liquid presentation form. With this technology, a major fraction of the active substance remains unused in the interior of the polymer. Moreover, part of the biocide is washed off as a result of weathering effects, and degenerated. In this case there are additional costs associated with production, and an increased pollution of the environment by the biocides.

As a result of the specific structure of the amine-modified siloxanes of the invention, which comprise at least one molecular unit with an amine-modified radical and at least one molecular unit with a hydrophilic radical, such as a polyether radical, it is possible for the biocidal structures to accumulate optimally at the surface, the site of action of the antimicrobial function, of the coating materials or workpieces, such as plastics, in order to achieve the maximum possible microbicidal activity. The migration of the compound (washing off, for example) ought in this case to be extremely low.

As stated, the amine-modified siloxanes have at least two molecular units with functionally modified radicals, specifically at least one siloxane unit which has been modified with an amine, and at least one siloxane unit which has been modified with a hydrophilic radical, such as a polyether. The two radicals, the hydrophilic radical and the amine-modified radical, may be present on one siloxane unit.

In one preferred embodiment the amine-modified siloxane is a siloxane having the following composition, the amine-modified siloxane comprising at least one molecular unit I

      (I)

and one molecular unit II

      (II)

where
X is independently at each occurrence an amine-modified radical $X^1$ or a hydrophilic radical $X^2$,
R independently at each occurrence is a saturated, unsaturated, straight-chain, branched or cyclic alkyl, alkenyl or alkoxy group having $C_1$ to $C_{18}$ carbon atoms, and where appropriate may be substituted;
a is an integer 0, 1 or 2;
b is an integer 1, 2 or 3, the sum of a and b being 1, 2 or 3;
c is an integer 0, 1, 2 or 3.

In one preferred embodiment the compound is one in which the radical $X^1$ is an amino-functional group of the following general formula

where $R^1$ and $R^2$ each independently of one another are a saturated or unsaturated, straight branched or cyclic alkylene or alkenylene group having $C_1$ to $C_{18}$ hydrocarbons, and where appropriate may be substituted.

With particular preference $R^1$ and $R^2$ are radicals with $C_1$ to $C_6$ hydrocarbons; in particular, $R^1$ and $R^2$ are each independently of one another a methylene, ethylene, propylene, butylene, pentylene or hexylene group.

The group $R^4$ may be identical or different and independently at each occurrence is hydrogen or a straight-chain, branched or cyclic $C_1$ to $C_{18}$ hydrocarbon group, which where appropriate may be substituted. $R^4$ is an alkyl or alkenyl group. Preferably $R^4$ independently at each occurrence is a $C_4$ to $C_{12}$ hydrocarbon group, more particularly a butyl, pentyl, hexyl, heptyl, octyl, nonyl, decyl, undecyl, and dodecyl group.

Thus in one embodiment of the present invention the amine-modified siloxane may be one in which at least one radical $R^4$ is not hydrogen, i.e., the amine group —$N(R^4)_2$ is a secondary or tertiary amine.

In a further embodiment the amine group may be a quaternary amine. Quaternary amine groups $(N(R^4)_3^+)$ are well known to the skilled worker, together with corresponding counterions, such as halide ions.

In a further preferred embodiment the hydrophilic radical $X^2$ of the molecular unit (I) is a hydrophilic polyether group with the following general formula:

where $R^1$ and $R^2$ are as defined above, $R^3$ is a hydrogen atom or a $C_1$ to $C_{18}$ straight-chain, branched or cyclic alkyl or alkenyl group, which where appropriate may be substituted; n is an integer 1 to 200, such as 1 to 50.

$R^3$ is preferably a group selected from methyl, ethyl, propyl, isopropyl, butyl, isobutyl, pentyl and hexyl.

Preference is given to the aforementioned alkyl, alkenyl or alkoxy group, that having 1 to 6 carbon atoms. More particularly preferably R, $R^3$ and $R^4$ each independently of one another are a radical from the group selected consisting of methyl, ethyl, propyl, isopropyl, butyl, isobutyl, pentyl, hexyl, methoxy, ethoxy, propoxy, isopropoxy, butoxy, isobutoxy, pentoxy and/or hexoxy.

In general, when a group or a radical may be substituted, suitable substituents independently of one another are one or more of, among others, C1 to C6 alkyl, C1 to C6 alkenyl, C1 to C6 alkoxy, OH, halogen, amino, nitro, substituted or unsubstituted acyl, substituted or unsubstituted aryl or heteroaryl, and the like, which where appropriate may be substituted again.

The molecular units (I) and (II) are preferably arranged linearly. In the case of a linear arrangement of the molecular units, c is 2 or 3 and the sum of a and b is likewise 2 or 3. In one preferred embodiment the ratio of the molecular units of the general formula (I) and (II) is between 1:200 to 20:1, with more particular preference between 10:25 to 20:10. In the molecular unit of the general formula (I) the ratio of the amine-modified radical $X^1$ to the hydrophilic radical $X^2$ is 1:10 to 10:1.

In the case of embodiments in which the molecular unit II is present with c=0 or 1, the molecules in question are branched siloxane molecules, in which these molecular units II with c=1 are branching elements with one branch and molecular units II with c=0 are branching elements with two branches; in other words, in the case of c=0, there are four molecular units on these branching elements. The fraction of molecular units II with c=0 or 1 is therefore very small, less than 3%, for example, such as 1%, in order to ensure sufficient low viscosity and high solubility.

In a further preferred embodiment the amine-modified siloxane has at least one molecular unit of the general formula (I) in which the radical X represents a radical $X^3$. This radical $X^3$ is in this case a crosslinkable group. More particularly this crosslinkable group $X^3$ represents a functional group which enters into interactions with the coating system or, on addition of the amine-modified polysiloxane of the invention, as microbicidal protecting agent, to the material compositions, enters into interactions with components of these materials and/or of the coating system. For example, $X^3$ is an acryloyl group, which can be reacted with radiation-curable UV coating systems; a hydroxyl group, which is able to react with the isocyanate groups in 2-component polyurethane coating materials (2-K-PU); an isocyanate group, for hydroxyl-containing coating materials (such as 2-K-PU or acrylate systems, for example); a polyunsaturated monocarboxylic acid, for alkyd systems; or an epoxide group for epoxy coating materials. With the aid of this functional group $X^3$ it is possible to bind the amine-modified siloxanes of the invention covalently to polymers of the coating system, and so the advantageous accumulation and optimum orientation of the amine-modified siloxane molecules of the invention at the surface of the coating film is maintained.

The coating systems or the polymer systems are typical coating systems and polymer systems of the kind well known to the skilled worker. Coating systems that may be mentioned here include, for example, surface-coating systems, systems based on polyurethanes, polyesters, alkyds, acrylates, epoxides, UV-crosslinkable systems, and baking varnishes.

The amine-modified siloxanes of the invention are used preferably in a concentration range from 0.05% to 20% w/w, preferably 0.2% to 8% w/w, in the coating systems or the polymer systems, in order to achieve the fungicidal or fungistatic effects.

The coating system with the protecting agents of the invention, the amine-modified siloxanes, can be applied by known methods to the workpieces. This includes methods such as spreading application, spray application, impregnation or dipping. If the amine-modified siloxanes are incorporated into polymer systems, binder systems or other systems for producing workpieces, this incorporation may take place by means of typical methods, such as mixing, stirring, kneading, etc.

The amine-modified siloxanes of the invention can also be used in conjunction with further known microbicides. Of course, it is also possible to use mixtures of two or more different amine-modified siloxanes.

PREPARATION PROCESS

Figure 1A:
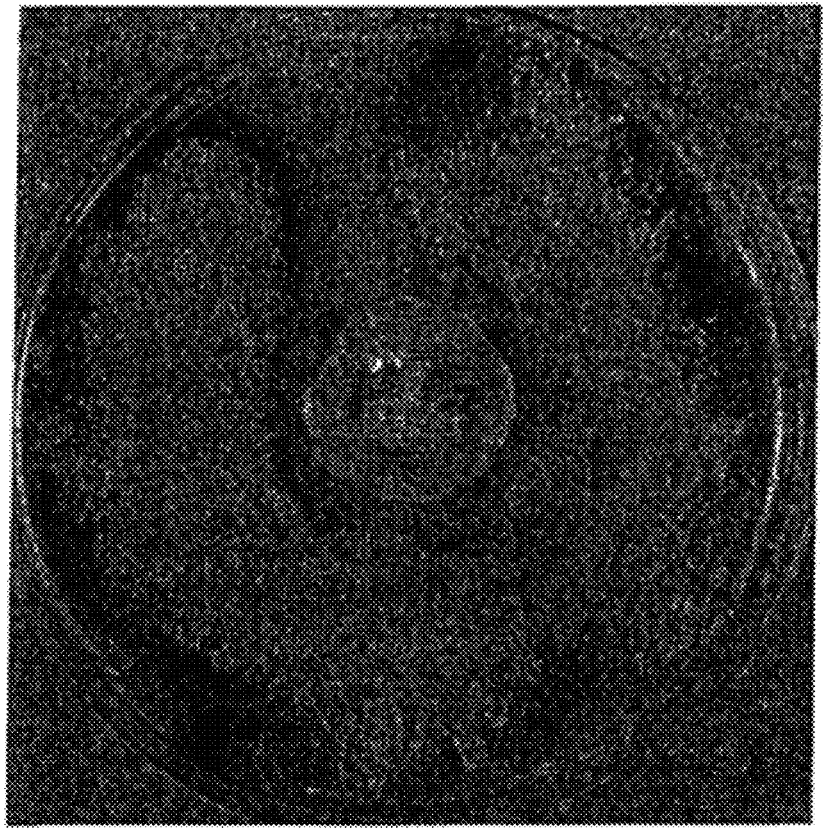
FIG. 1 shows the results of the culture plates inoculated in example 8. A: plate with the amine-modified compound of example 1; B: plate with the inventive compound obtained in example 2; C: plate with the inventive compound obtained in example 3; D: plate with the inventive compound, obtained in example 4, which has been incorporated into a coating system as per example 6; E: control, coating system without addition of an inventive compound.
Figure 1B:
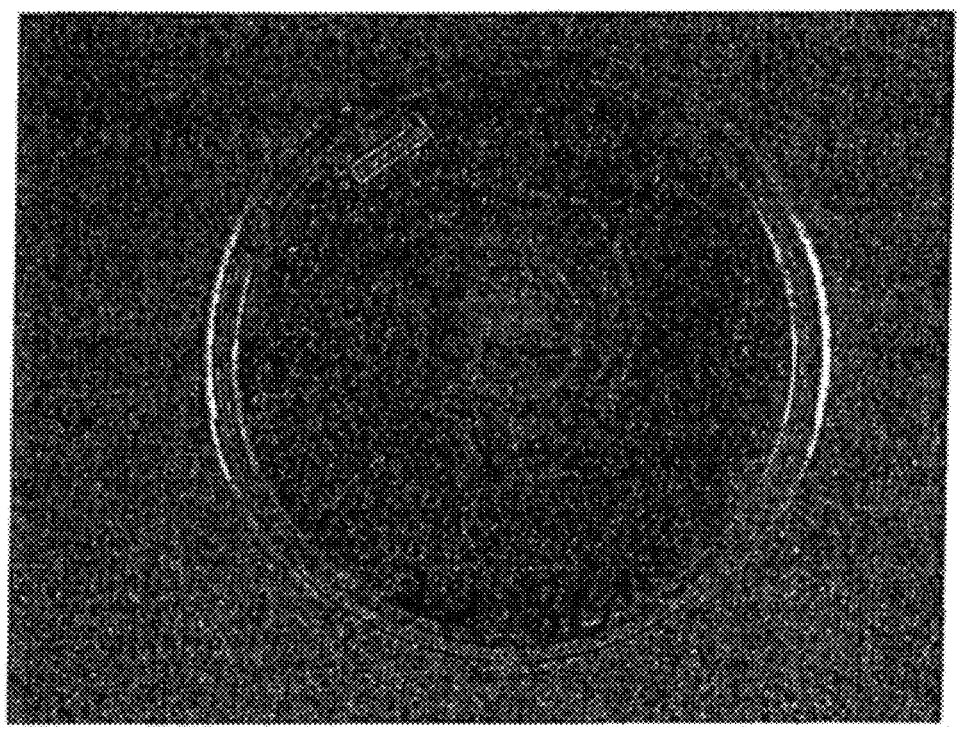
Figure 1C:
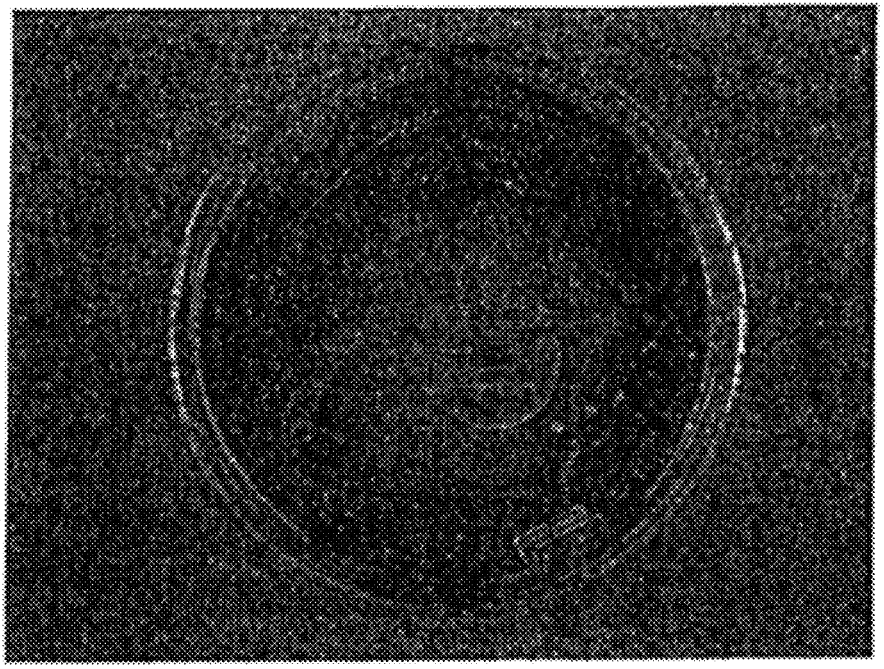
Figure 1D:
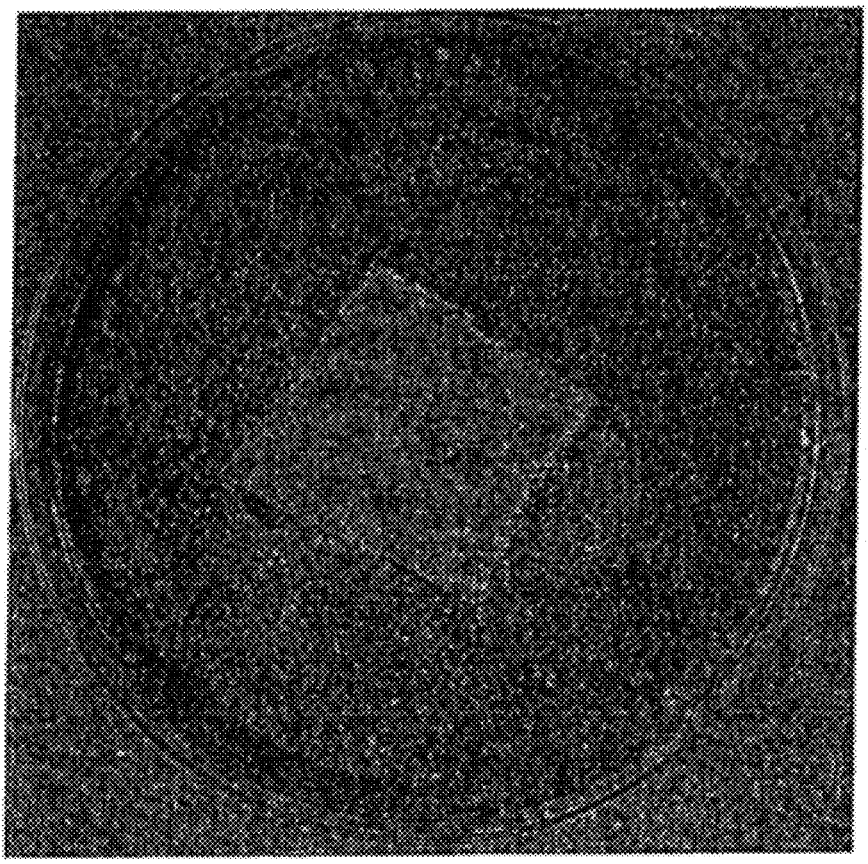
Figure 1E:
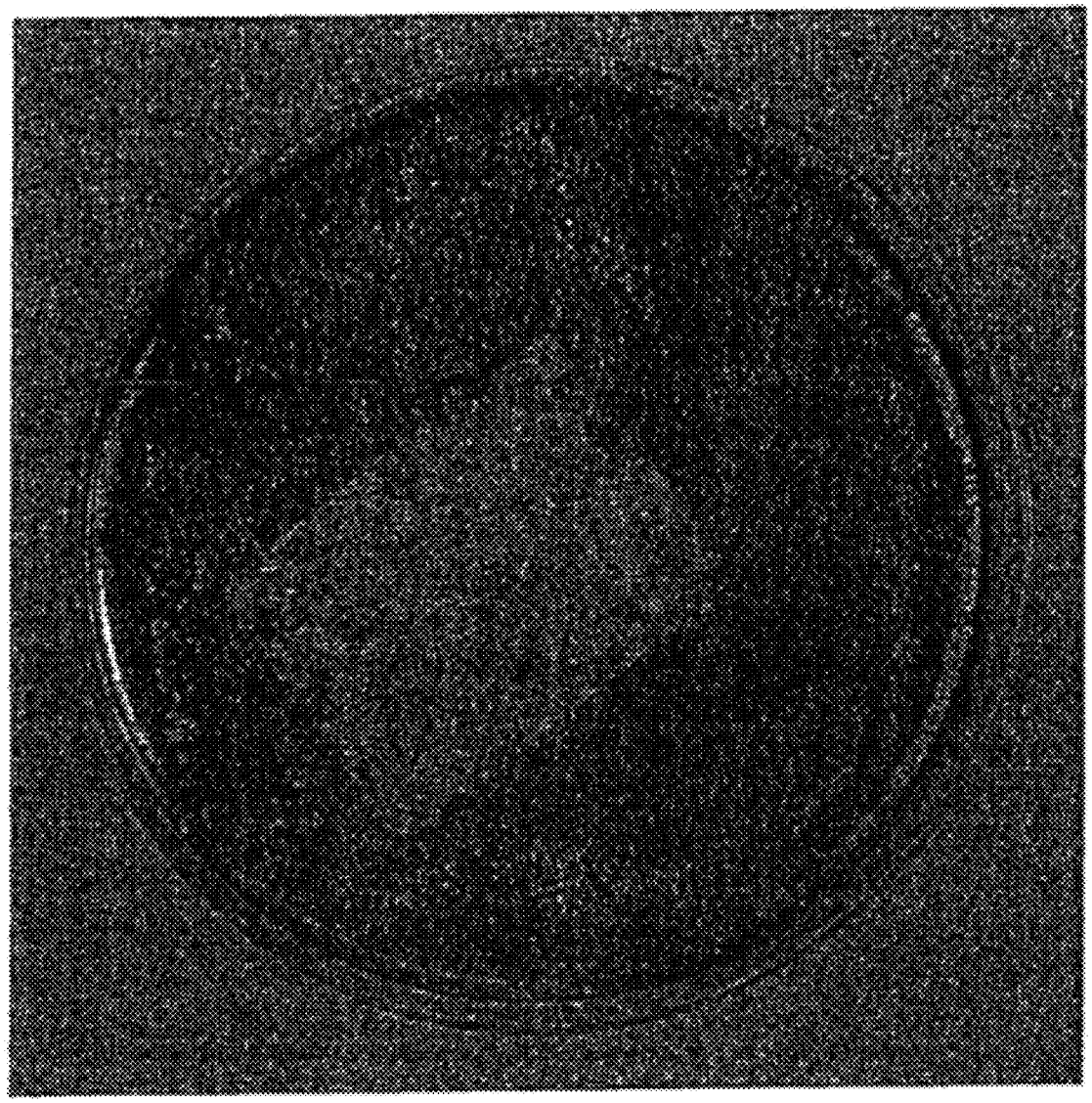
Figure 2:
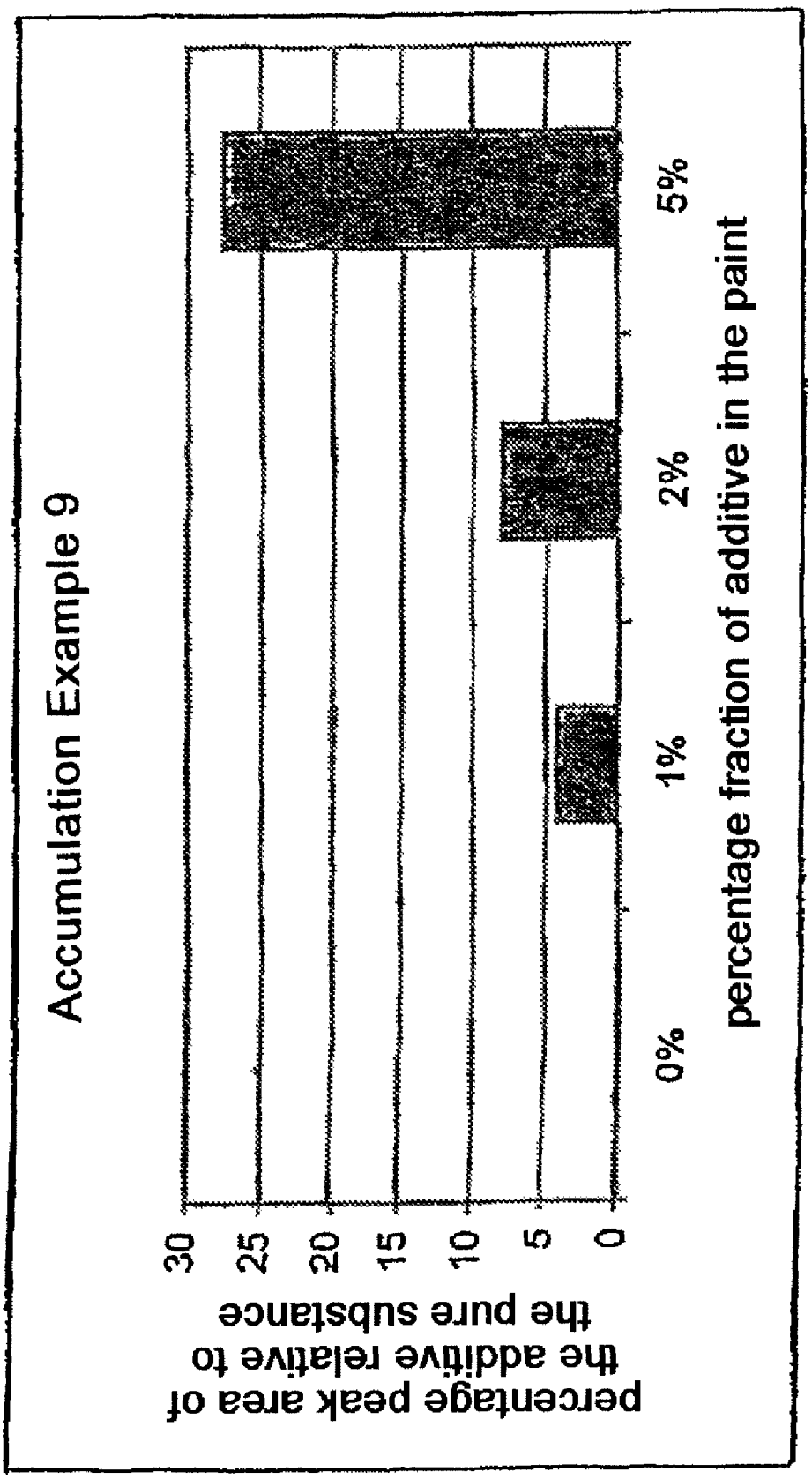
FIG. 2 shows the results of the ATR-FTIR analysis of a coating system according to example 5. The figure shows the percentage peak area of the additive relative to the pure substance. The accumulation of the amine-modified siloxanes at the surface of the cured coating films is clearly in evidence.

The siloxane described is prepared in two reaction steps. Starting materials used are unbranched hydrogenmethyl-co-dimethylsiloxanes with different levels of Si—H-functional groups.

In the first step the hydrophilic group, such as polyethers and epoxy compounds, with allyl function is adducted with the Si—H groups. In order to avoid possible side reactions of hydroxyl groups with the Si—H groups, the reaction is carried out under nitrogen, using hexachloroplatinic acid as catalyst. The reaction is carried out at 90-110° C. for 4 hours and proceeds quantitatively. It is over when Si—H bonds can no longer be detected by means of FTIR spectroscopy.

In the second step, the epoxide ring is opened by means of the amine. This requires temperatures of around 70-90° C. The reaction can be monitored by way of the decrease in the epoxide number. In the product, free amine is no longer detectable by means of thin-layer chromatography. The molar mass of the amine-modified polysiloxanes is of the order of 500-100 000 g/mol, preferably 500-10 000 g/mol.

In this reaction regime there is no change in the chain length of the siloxane, since the modifications of the hydrogenmethyl-co-dimethylsiloxane take place in the side chains and terminally. The construction of a new siloxane backbone of silane monomers (such as amino-functional and/or polyether-functional chlorosilanes, methoxysiloxanes, and silanols, for example) is unsuitable. Firstly, low molecular mass elimination products such as hydrogen chloride, water or methanol must be removed from the system; secondly, unwanted side reactions of the epoxide group are likely.

EXAMPLES

A. Preparation of Amine-Modified Siloxanes

Example 1

A three-neck flask with dropping funnel, internal thermometer, and reflux condenser is charged with 4.400 g of allyl polyether (molar mass 1100 g/mol) and 1.368 g of allyl glycidyl ether. The mixture is admixed with 70 mg of platinum catalyst solution (hexachloroplatinic acid in isopropanol, 1.27% strength) and heated to 40-60° C. 4.324 g of hydrogenmethyl-co-dimethylsiloxane (3.7 mmol Si—H/g) are added dropwise with stirring. The reaction solution is stirred at 90-100° C. for 4 h. After it is cooled to 40-60° C., with stirring, 2.898 g of dioctylamine are dissolved and added dropwise in 20 ml of ethanol. The mixture is heated to the boiling point of the solvent and stirred under reflux for 2 hours. Subsequently the solvent is removed under reduced pressure.

Example 2

A three-neck flask with dropping funnel, internal thermometer, and reflux condenser is charged with 4.200 g of allyl polyether (molar mass 350 g/mol) and 0.456 g of allyl glycidyl ether. The mixture is admixed with 60 mg of platinum catalyst solution (hexachloroplatinic acid in isopropanol, 1.27% strength) and heated to 40-60° C. 4.324 g of hydrogenmethyl-co-dimethylsiloxane (3.7 mmol Si—H/g) are added dropwise with stirring. The reaction solution is stirred at 90-100° C. for 4 h. After it is cooled to 40-60° C., with stirring, 0.966 g of dioctylamine, in solution in 20 ml of ethanol, is added dropwise. The mixture is heated to the boiling point of the solvent and stirred under reflux for 2 hours. Subsequently the solvent is removed under reduced pressure.

Example 3

A three-neck flask with dropping funnel, internal thermometer, and reflux condenser is charged with 1.400 g of allyl polyether (molar mass 350 g/mol) and 1.368 g of allyl glycidyl ether. The mixture is admixed with 60 mg of platinum catalyst solution (hexachloroplatinic acid in isopropanol, 1.27% strength) and heated to 40-60° C. 4.324 g of hydrogenmethyl-co-dimethylsiloxane (3.7 mmol Si—H/g) are added dropwise with stirring. The reaction solution is stirred at 90-100° C. for 4 h. After it is cooled to 40-60° C., with stirring, 2.898 g of dioctylamine, in solution in 20 ml of ethanol, are added dropwise. The mixture is heated to the boiling point of the solvent and stirred under reflux for 2 hours. Subsequently the solvent is removed under reduced pressure.

Example 4

A three-neck flask with dropping funnel, internal thermometer, and reflux condenser is charged with 4.000 g of allyl polyether (molar mass 500 g/mol) and 0.912 g of allyl glycidyl ether. The mixture is admixed with 70 mg of platinum catalyst solution (hexachloroplatinic acid in isopropanol, 1.27% strength) and heated to 40-60° C. 4.324 g of hydrogenmethyl-co-dimethylsiloxane (3.7 mmol Si—H/g) are added dropwise with stirring. The reaction solution is stirred at 90-100° C. for 4 h. After it is cooled to 40-60° C., with stirring, 1.932 g of dioctylamine, in solution in 20 ml of ethanol, are added dropwise. The mixture is heated to the boiling point of the solvent and stirred under reflux for 2 hours. Subsequently the solvent is removed under reduced pressure.

B. Coating Systems Comprising Amine-Modified Siloxanes

Example 5

| Coating system with following composition: | |
| --- | --- |
| styrene acrylate dispersion | 87.6% by weight |
| polyether-modified dimethylpolysiloxane copolymer | 0.5% by weight |
| defoamer based on polysiloxanes and hydrophobic solids in polyglycol | 0.4% by weight |
| butyl diglycol | 2.0% by weight |
| demineralized water | 6.5% by weight |
| amine-modified polyether siloxane from ex. 3 | 3.0% by weight |

Example 6

| Coating system with following composition: | |
| --- | --- |
| approximately 50% aqueous dispersion of a copolymer based on 2-ethylhexyl acrylate and methyl methacrylate | 90.7% by weight |
| defoamer based on polysiloxanes and hydrophobic solids in polyglycol | 0.4% by weight |
| butyl diglycol | 2.0% by weight |
| wetting additive based on modified polysiloxanes | 0.5% by weight |
| PU thickener | 1.4% by weight |
| amine-modified polyethersiloxane from ex. 1 | 5.0% by weight |

Example 7

| Coating system with following composition: | |
| --- | --- |
| bisphenol A epoxy acrylate | 65.9% by weight |
| tripropylene glycol diacrylate | 25.6% by weight |
| polyether-modified dimethylpolysiloxane copolymer | 1.5% by weight |
| benzophenone | 2.0% by weight |
| 1-hydroxycyclohexyl phenyl ketone | 2.0% by weight |
| amine-modified polyethersiloxane from ex. 2 | 3.0% by weight |

C. Presentation of the Microbicidal Properties

Example 8

The product from examples 1 to 3 is used as the pure substance, the product from example 4 as a 5% addition in a coating system according to example 6. The samples are added dropwise to or placed on an agar (2%)/biomalt (2%) nutrient medium in Petri dishes, inoculated with a fungal spore suspension (*Aspergillus versicolor, Cladosporium cladosporoides, Alternaria alternata*) and incubated at 23° C. and a relative atmospheric humidity ≧90%. Whereas fungal colonies become visible on the reference system (coating system according to example 6 without additive), without amine-modified additive, after just one week, the sample with the amine-modified polyethersiloxane is not infested even after 4 weeks.

Example 9

The product from example 1 is incorporated into a coating system according to example 5 (with omission of other siloxane additives) at 1%, 2%, and 5% by weight. In parallel, a reference coating material without additive is prepared. The surfaces of the cured films are investigated by means of ATR-FTIR spectroscopy. With this method, only a few μm of the coating surface are considered. The surfaces differ precisely in the signals which can be assigned to the amine-modified additive. The peak areas from the differential spectrum (coating with additive minus reference coating material) are compared in relation to peak areas of the additive as the pure substance with the amount employed in each case. Here it becomes clear that the use of 1% of additive in the coating material accounts for more than 4% of the peak area of the pure substance. Consequently the substance is not uniformly distributed but has instead accumulated at the surface of the coating film. The effect is intensified as the amount employed increases.

The invention claimed is:

1. A method of protecting a surface of a workpiece, comprising the step of coating at least one surface of a workpiece with one or more amine-modified siloxanes, the one or more amine-modified siloxanes having
at least one molecular unit I $$R_a X_b \mathrm{SiO} \frac{(4-a-b)}{2}$$ (I)

and one molecular unit II $$R_c \mathrm{SiO} \frac{(4-c)}{2}$$ (II)

where
X independently at each occurrence is an amine-modified radical $X^1$ or a hydrophilic radical $X^2$, and $X^1$ and $X^2$ occur at least once in the one or more amine-modified siloxanes, wherein the amine-modified radical $X^1$ is an
amino-functional group of the following general formula

—$R^1$—O—$R^2$—C(OH)H—CH$_2$—N($R^4$)$_2$ where $R^1$ and $R^2$ each independently of one another are a saturated or unsaturated, straight, branched or cyclic alkylene or alkenylene group having $C_1$ to $C_{18}$ carbon atom(s), and where appropriate may be substituted; and
$R^4$ independently at each occurrence is hydrogen, a straight-chain, branched or cyclic $C_1$ to $C_{18}$ alkyl or alkenyl group, which where appropriate may be substituted;
R independently at each occurrence is a saturated, unsaturated, straight-chain, branched or cyclic alkyl, alkenyl or alkoxy group having $C_1$ to $C_{18}$ carbon atoms, and where appropriate may be substituted;
a is an integer 0, 1 or 2;
b is an integer 1, 2 or 3, where a sum of a and b is 1, 2 or 3;
c is an integer 0, 1, 2 or 3, wherein said coating step forms a surface coating with biocidal properties for protecting said workpiece.

2. The method as claimed in claim 1, wherein at least one $R^4$ is not hydrogen.

3. The method as claimed in claim 1, wherein $R^4$ independently at each occurrence is a straight-chain, branched or cyclic $C_1$ to $C_{18}$ alkyl or alkenyl group.

4. The method as claimed in claim 1, wherein the hydrophilic radical $X^2$ is a hydrophilic polyether group with the following general formula —$R^1$—(O—$R^2$—)$_n$—O—$R^3$ where $R^1$ and $R^2$ independently of one another are an alkylene or alkenylene group having 1 to 18 hydrocarbons,
$R^3$ is a hydrogen atom or a substituted or unsubstituted straight-chain, branched or cyclic $C_1$ to $C_{18}$ alkyl or alkenyl group; and
n is an integer 1 to 200.

5. The method as claimed in claim 4, wherein $R^1$, $R^2$, and $R^3$ each independently of one another have 1 to 6 carbon atoms.

6. The method as claimed in claim 5 wherein $R^1$ and $R^2$ each independently of one another are a methylene, ethylene, propylene, butylene, pentylene or hexylene group.

7. The method as claimed in any claim 5, wherein $R^3$ independently at each occurrence is a group selected from methyl, ethyl, propyl, isopropyl, butyl, isobutyl, pentyl, and hexyl.

8. The method as claimed in claim 1, wherein R independently at each occurrence has 1 to 6 carbon atoms.

9. The method as claimed in claim 8, wherein R independently at each occurrence is selected from the group consisting of methyl, ethyl, propyl, isopropyl, butyl, isobutyl, pentyl, hexyl, methoxy, ethoxy, propoxy, isopropoxy, butoxy, isobutoxy, pentoxy, and hexoxy.

10. The method as claimed in claim 1 wherein $R^1$ and $R^2$ each independently of one another are a methylene, ethylene, propylene, butylene, pentylene or hexylene group.

11. The method as claimed in claim 1 wherein $R^4$ independently at each occurrence is a $C_4$ to $C_{12}$ hydrocarbon atom group.

12. The method as claimed in claim 1, wherein the one or more amine-modified siloxanes has a molar mass of between 500 and 100,000 g/mol.

13. The method as claimed in claim 1, wherein a ratio of molecular units of the general formulas (I) and (II) is between 1:200 to 20:1.

14. The method as claimed in claim 1, wherein a ratio of the amine-modified radical $X^1$ to the hydrophilic radical $X^2$ is 1:10 to 10:1.

15. The method as claimed in claim 1, wherein the one or more amine-modified siloxanes has at least one molecular unit I in which X is a radical crosslinkable group $X^3$.

16. The method as claimed in claim 1, wherein the molecular units I and II are arranged linearly and c is 2 or 3 and a+b is 2 or 3.

17. The method use as claimed in claim 16, wherein said workpiece includes lignocellulosic materials.

18. The method as claimed in claim 1, wherein said one or more amine-modified siloxanes includes a plurality of different amine-modified siloxanes.

19. The method as claimed in claim 1, wherein said step of coating is performed in combination with one or more different microbicides.

20. The method of claim 19 wherein said one or more different microbicides includes at least one fungicide.

21. The method use as claimed claim 1, wherein said one or more amine modified siloxanes are used in said coating step using a coating composition for coating surfaces.

22. The method of claim 1 wherein said step of coating is performed by a process of spreading, spraying, dipping, vacuum impregnating, pressure impregnating, or tank pressure impregnating.

23. The method as claimed in claim 1, wherein $R^1$ and $R^2$ each independently of one another have 1 to 6 carbon atoms.

24. The method as claimed in claim 23, wherein $R^1$ and $R^2$ each independently of one another are a methylene, ethylene, propylene, butylene, pentylene or hexylene group.

25. A method of treating surfaces of workpieces against infestation by fungi, comprising the step of applying to at least one surface of a workpiece a protecting agent comprising one or more amine-modified siloxanes having at least one molecular unit I $$\frac{R_a X_b SiO(4-a-b)}{2} \qquad (I)$$

and one molecular unit II $$\frac{R_c SiO(4-c)}{2} \qquad (II)$$

where

X independently at each occurrence is an amine-modified radical $X^1$ or a hydrophilic radical $X^2$, and $X^1$ and $X^2$ occur at least once in the one or more amine-modified siloxanes, wherein the amine-modified radical $X^1$ is an amino-functional group of the following general formula $$-R^1-O-R^2-C(OH)H-CH_2-N(R^4)_2$$

where $R^1$ and $R^2$ each independently of one another are a saturated or unsaturated, straight, branched or cyclic alkylene or alkenylene group having $C_1$ to $C_{18}$ carbon atom(s), and where appropriate may be substituted; and $R^4$ independently at each occurrence is hydrogen, a straight-chain, branched or cyclic $C_1$ to $C_{18}$ alkyl or alkenyl group, which where appropriate may be substituted;

R independently at each occurrence is a saturated, unsaturated, straight-chain, branched or cyclic alkyl, alkenyl or alkoxy group having $C_1$ to $C_{18}$ carbon atoms, and where appropriate may be substituted;

a is an integer 0, 1 or 2;

b is an integer 1, 2 or 3, the sum of a and b being 1, 2 or 3;

c is an integer 0, 1, 2 or 3.

26. The method as claimed in claim 25, wherein the protecting agent is applied by spreading, spraying, dipping, vacuum impregnating, pressure impregnating or tank pressure impregnating.

* * * * *